United States Patent [19]

Kwoh et al.

[11] Patent Number: 5,055,393
[45] Date of Patent: Oct. 8, 1991

[54] PRENATAL SEX DETERMINATION OF BOVINE CELLS USING MALE-SPECIFIC OLIGONUCLEOTIDES

[75] Inventors: Deborah Y. Kwoh, Carlsbad; Thomas R. Gingeras, Encinitas, both of Calif.

[73] Assignee: Salk Institute Biotechnology/Industrial Associates, Inc., San Diego, Calif.

[21] Appl. No.: 366,153

[22] Filed: Jun. 13, 1989

[51] Int. Cl.$^5$ .................. C12P 19/34; C12Q 7/68; C07H 15/12; C07H 17/00
[52] U.S. Cl. .................. 435/6; 435/91; 536/26; 536/27; 536/28; 436/501; 436/94
[58] Field of Search ............ 435/6, 172.3, 91; 536/26, 27, 28; 436/501, 94; 935/77, 78

[56] References Cited

U.S. PATENT DOCUMENTS

| | | |
|---|---|---|
| 4,683,195 | 7/1987 | Mullis et al. |
| 4,683,202 | 7/1987 | Mullis ............................ 435/91 |
| 4,769,319 | 9/1988 | Ellis et al. ....................... 435/6 |

FOREIGN PATENT DOCUMENTS

| | | |
|---|---|---|
| 0235046 | 9/1987 | European Pat. Off. |
| 8607095 | 12/1986 | PCT Int'l Appl. |
| 8801300 | 2/1988 | PCT Int'l Appl. |
| 8902440 | 3/1989 | PCT Int'l Appl. |

OTHER PUBLICATIONS

Bondioli et al., "The Use of Male-Specific Chromosomal DNA Fragments to Determine the Sex of Bovine Preimplantation Embryos", *Therigenology*, 31:1, 1989, pp. 95–104.

Ellis et al., "Sex Determination of Bovine Embryos Using Male-Specific DNA Probes", *Theriogeonology*, 29:1, 1988, p. 242.

Herr et al., "Accuracy of a rapid Y-Chromosome-Detecting Bovine Embryo Sexing Assay", personal communication.

Herr et al., "Field Implementation of a Rapid Y-Chromosome-Detecting Bovine Embryo Sexing Assay", personal communication.

Handyside et al., "Biopsy of Human Preimplantation Embryos and Sexing by DNA Amplification", *The Lancet*, Feb. 18, 1989, pp. 347–349.

Kirszenbaum et al., "PCR Sexing Bovine Embryos Using Y Chromosome Specific Sequences", *Journal of Cellular Biochemistry Abstracts*, Supplement 13E, 1989, WH200, p. 293.

Leonard et al., "Sexing Bovine Embryos Using Y Chromosome Specific DNA Probe", *Theriogenology*, 27:1, 1987, p. 248.

Li et al., "Amplification and Analysis of DNA Sequences in Single Human Sperm and Diploid Cells", *Nature*, 35:29, 1988, pp. 414–417.

*Primary Examiner*—Robert A. Wax
*Assistant Examiner*—Eric Steffe
*Attorney, Agent, or Firm*—Fitch, Even, Tabin & Flannery

[57] ABSTRACT

Compositions and methods are provided for determining the sex of Bovine embryos and fetuses employing male-specific oligonucleotides in nucleic acid probe hybridization assay methods to assay the genomic DNA of embryonic or fetal cells for the presence of male-specific sequences.

11 Claims, 5 Drawing Sheets

FIG. IA

| Cell # | DNA conc. |
|---|---|
| 50 | 0.5 ng |
| 10 | 0.1 ng |
| 2 | 0.02 ng |
| 1 | 0.01 ng |
| 100 | 1 ng female |

FIG. IB

| Cell # | DNA conc. |
|---|---|
| 50 | 0.5 ng |
| 10 | 0.1 ng |
| 2 | 0.02 ng |
| 1 | 0.01 ng |
| 100 | 1 ng female |

FIG. IC

| Cell # | DNA conc. |
|---|---|
| 100 | 1 ng female |
| 25 | 0.25 ng |
| 20 | 0.20 ng |
| 15 | 0.15 ng |
| 10 | 0.10 ng |
| 5 | 0.05 ng |
| 2.5 | 0.025 ng |

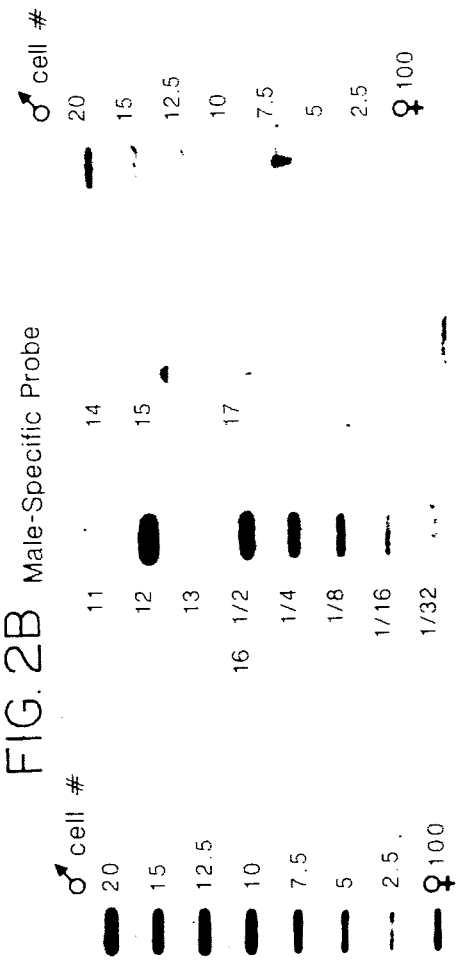
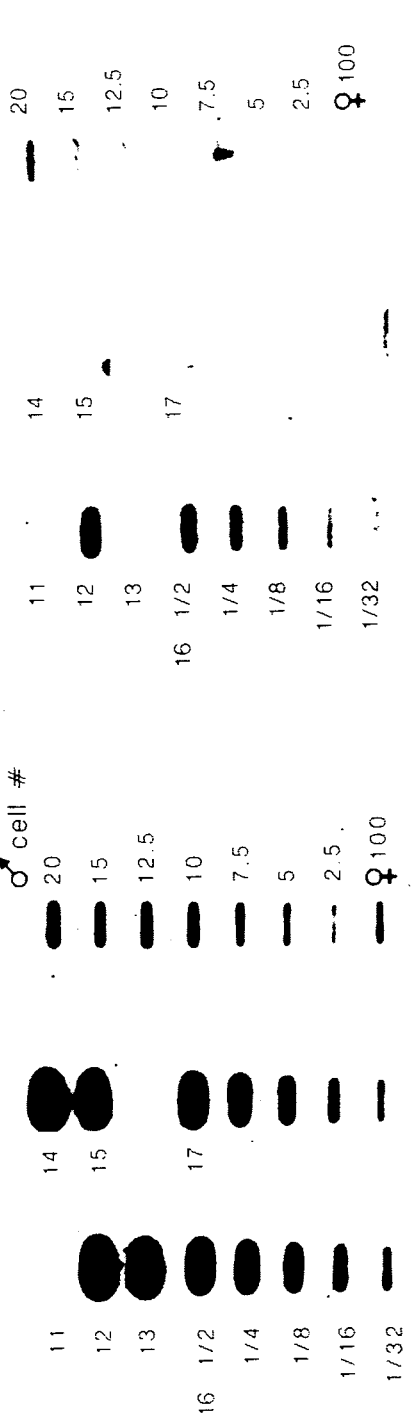
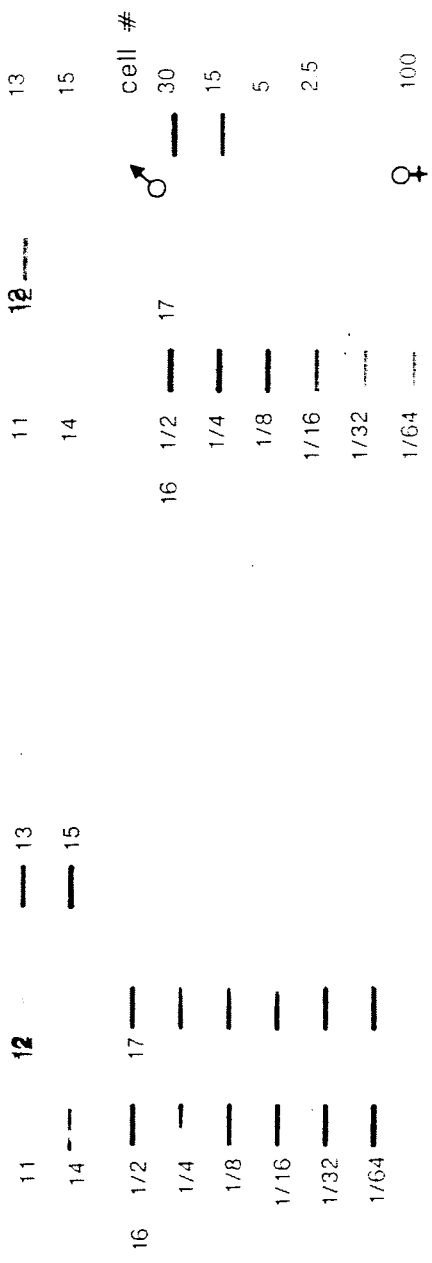

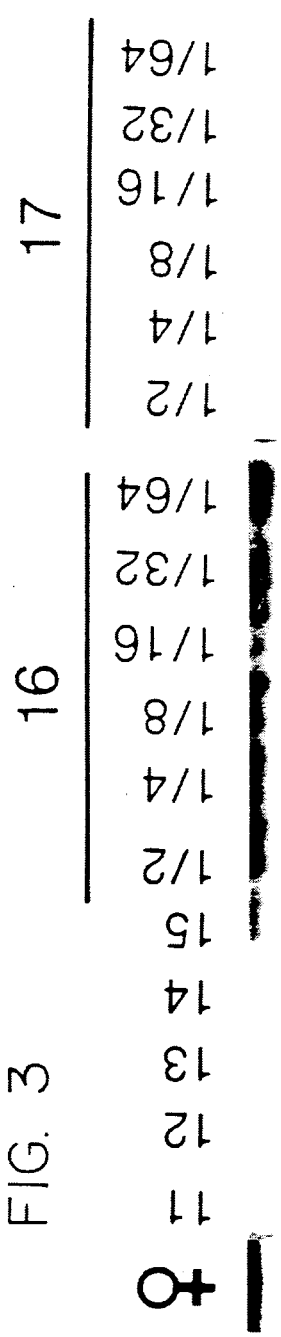
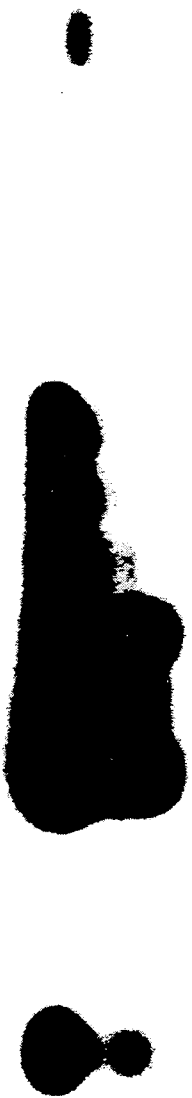
FIG. 3
Male-Specific Probe

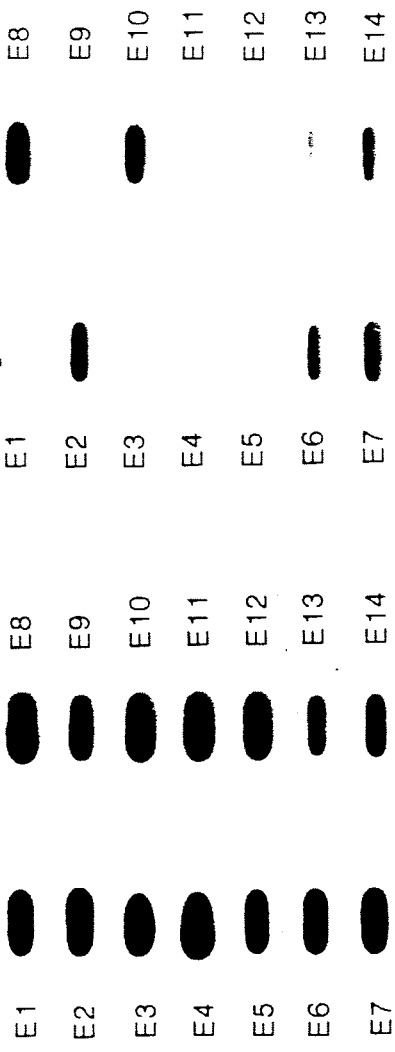
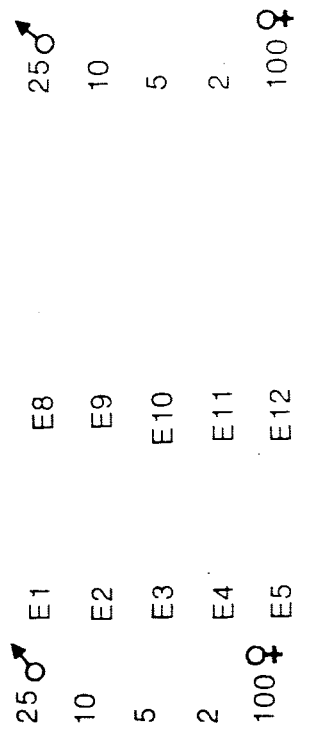
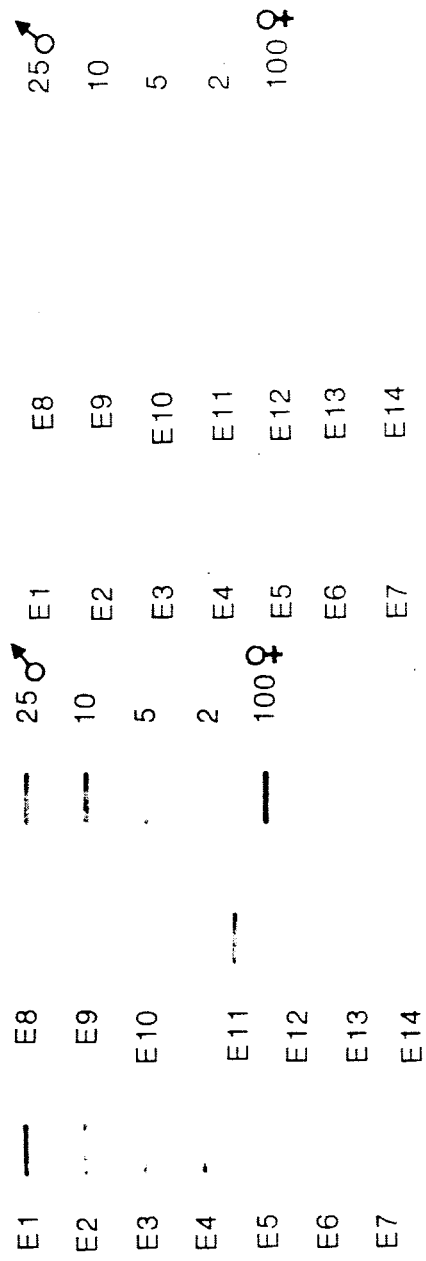

PRENATAL SEX DETERMINATION OF BOVINE CELLS USING MALE-SPECIFIC OLIGONUCLEOTIDES

FIELD OF THE INVENTION

The present invention relates to sex determination. More particularly, the present invention provides a method and means for the determination of the sex of bovine embryos or fetuses shortly after conception. Sexing is based upon the detection of DNA sequences that are present only on the Y chromosome, using labeled oligonucleotides capable of hybridizing with such male-specific sequences.

BACKGROUND OF THE INVENTION

The ability to predetermine the sex of offspring from embryo transfer has been the goal of the embryo transfer industry for a long time. The most desirable method to achieve this goal would be insemination of donors with a homogenous population of either X-chromosome bearing or Y-chromosome bearing spermatozoa, but at present, methods to separate spermatozoa into these populations are not available. Therefore, currently the next best method, determination of the sex of the preimplantation embryos before transfer to a recipient is pursued.

The accurate determination of the sex of bovine embryos shortly after fertilization provides numerous advantages in the dairy and livestock industries. The economic efficiency of livestock and dairy operations is significantly improved by allowing gestation to continue beyond the very early stage only for embryos of the desired sex. Especially with the advent of embryo transfer technology, the goal is to sex embryos routinely prior to transfer into female hosts. In this way all risks and expenses associated with pregnancy with an embryo of undesired sex can be avoided. It is further desirable to shorten the time required for the determination of the sex of an embryo, thereby removing the need to freeze the embryos while the sex determination is being made and thus increasing the overall success rate of the transfers.

The sex of mammalian embryos is determined by the presence or absence of the Y chromosome. Therefore, the determination of the sex of embryos is based upon detection of DNA sequences that are present only on the Y chromosome. In order to increase the sensitivity of the detection methods, usually repetitive male-specific sequences are sought for. Nucleic acid-based sex determination is generally based upon hybridization of DNA obtained from pre-implantation embryos with repetitive male-specific sequences, and detection of the hybridization signal, for example by using radioactive isotopes. A positive hybridization signal indicates that the embryo is male.

Nucleic acid hybridization probes for sexing of bovine embryos are disclosed in the U.S. Pat. No. 4,769,319 and in the PCT Patent Application Publication No. WO 86/0795, both assigned to Salk Institute Biotechnology Industrial Associates, Inc. These probes were based on three repetitive, male-specific bovine chromosomal DNA fragments. The accuracy of sex determination was virtually 100%, using an amount of DNA equal to the amount obtained from 4 or fewer embryonic cells, and the test took approximately six days. The length of time required to conduct the procedure was primarily due to the length of time required to detect a hybridization signal. The hybridization probes used in the examples were radioactively labeled.

Identification and cloning of repeated sequences that are specific for the bovine Y chromosome are reported by Leonard et.al., *Theriogenology* 27, 248 (1987) (abstract). A not identified biotinylated bovine Y-chromosome specific DNA probe was in situ hybridized with DNA obtained from about 10–20 trophoblastic cells biopsied from 7–8-day old bovine embryos, and the hybridization signal was detected using an immunocytochemical technique. "Clear cut" results were obtained only on 57% of the performed biopsies, and, based upon these results, the accuracy of sexing was estimated to be 95%. The sexing assay required 30 hours.

The use of a 49 of oligonucleotide as a male-specific probe for sexing embryos of ruminants is described in the European Patent Application Publication No. 0,235,046. In some experiments Southern hybridization was performed and the hybridization signal was detected with radioactive methods essentially within the time frame discussed in connection with the above-identified US patent and PCT patent application. Alternatively, in situ hybridization and detection with non-radioactive (biotinylation) methods were performed.

The PCT Patent Application Publication No. WO 88/01300 discloses a 307 nucleotides long Y-chromosome-specific DNA sequence which is universally conserved amongst ruminant animals (BRY.1). This sequence was used for discrimination between male and female calves and sheep, respectively.

The time requirement of the bovine sexing assays can be reduced sufficiently by replacing the lengthy hybridization and radioactive detection techniques with an assay based on in vitro target amplification by polymerase chain reaction (PCR) and nonradioactive detection. The PCR technique is, for example described in the U.S. Pat. Nos. 4,683,202 and 4,683,195. The process comprises treating separate complementary strands of a nucleic acid comprising one or more specific sequence(s) to be amplified, with a molar excess of two oligonucleotide primers, and extending the primers to form complementary primer extension products which act as templates for synthesizing the desired nucleic acid sequence. The primers must be sufficiently complementary to hybridize with the different strands of each specific sequence the amplification of which is desired. The process can be repeated as often as necessary to produce the desired amount of the sequence.

Sexing of bovine embryos using Y-chromosome-specific sequences and PCR amplification, is reported by Kirszenbaum et.al., *Journal of Cellular Biochemistry* Supplement 13E, 293 (1989) (abstract of a poster presented on the UCLA Symposia on Molecular & Cellular Biology, 18th Annual Meetings, April 3-April 24, 1989). The authors used a 50 of male-specific probe designated pBCl.2 for sexing bovine embryos. Ten embryo biopsies of about 50 cells were subjected to 40 cycles of PCR amplification, 4 of which were identified as male.

SUMMARY OF THE INVENTION

We have developed short oligonucleotide probes that efficiently hybridize with repeated male-specific sequences of bovine chromosomal DNA (target), and thereby permit the determination of the sex of bovine embryos or fetuses. The sensitivity of the method was substantially increased by using non-radioactive detection techniques and by using target DNA sequence amplification by polymerase chain reaction (PCR).

In one aspect, the present invention relates to an oligonucleotide having or containing substantially the same sequence as that of a DNA selected from the group consisting of

CCTTGCACAGTCGCTAGGGCACA 84-151),

ATCCAGGCTGGCTCCTGCCCTCGGT-CAAGA (87-371) and

GTTCCGCCCTTCCTGAAGTGCCCGT-CTAAA (87-373).

Under optimized conditions an assay using PCR amplification and non-radioactive detection technique can be completed within 5-6 hours.

In another aspect, this invention relates to a method for determining the sex of an embryo or fetus of a species of genus Bos, comprising:

(a) contacting chromosomal DNA extracted from at least 100 cells of said embryo or fetus under hybridization conditions with one or more hybridization probes labeled with a detectable marker, at least one of said probes having or containing substantially the same sequence as that of a DNA selected from the group consisting of

CCTTGCACAGTCGCTAGGGCACA (87-151),

CCTTGCACAGTCGCTAGGGCACA (87-151), and

GTTCCGCCCTTCCTGAAGTGCCCGT-CTAAA (87-373), and (b) ascertaining whether hybridization above background occurs between said chromosomal DNA and said hybridization probe or probes.

The hybridization probes are preferably non-radioactively labeled, for example with alkaline phosphatase.

In a further aspect, the invention concerns a method for determining the sex of an embryo or fetus of a species of genus Bos, comprising:

(a) amplifying a male-specific segment of chromosomal DNA of said embryo or fetus, by (i) separating complementary strands of said chromosomal DNA, (ii) annealing the separated complementary strands, respectively with a 5' and a 3' oligonucleotide primer having sufficient complementarity with said strand of said male-specific segment of said chromosomal DNA to hybridize therewith, (iii) incubating the annealed DNA with DNA polymerase whereby the 5' and 3' oligonucleotide primers are extended through said male-specific segment of said chromosomal DNA, if present, and repeating steps (a) (i)-(iii) as many times as required to obtain a desired level of said double-stranded male-specific segment of said chromosomal DNA, and (b) detecting the amplified, double-stranded male-specific segment in said chromosomal DNA.

The amplified male-specific segment is preferably detected by (i) contacting said amplified chromosomal DNA under hybridization conditions with a hybridization probe labeled with a detectable marker, and (ii) ascertaining whether hybridization above background between said amplified chromosomal DNA of the embryo or fetus and the hybridization probe, wherein said 5' and 3' oligonucleotides and said hybridization probe have or contain substantially the same sequences as those of the DNAs selected from the group consisting of (A) a 5' primer of sequence

CACAGTCGCCAGGGCACAGGGCTG (86-429)

a 3' primer of sequence

AGCCCTGTGCTCTGGCGACTGTGAAACC (87-374)

a detection oligonucleotide of sequence

CCTTGCACAGTCGCTAGGGCACA (87-151), (B) a 5' primer of sequence

AAGACCCTGACAAACACTCCTGAGC-CCACC (87-331)

a 3' primer of sequence
a detection oligonucleotide of sequence

ATCCAGGCTGGCTCCTGCCCTCGGT-CAAGA (87-371), and (C) a 5' primer of sequence

CCTCCCCTTGTTCAAACGCCCGGAAT-CATT (87-334)

a 3' primer of sequence

TGCTTGACTGCAGGGACC-GAGAGGTTTGGG (87-372)

a detection oligonucleotide of sequence

GTTCCGCCCTTCCTGAAGTGCCCGTCTAAA (87-373).

According to a particular embodiment of the invention, simultaneously with the amplification of a male-specific segment of the chromosomal DNA, a non-sex-specific segment is also co-amplified, wherein the non-sex-specific 5' and 3' primers and detection oligonucleotides are selected from the group consisting of (D) a 5' primer of sequence

AGGTCGCGAGATTGGTCGCTAGGT-CATGCA (88-41)

a 3' primer of sequence

AAGACCTCGAGAGACCCTCTTCAACACGT (88-42)

a detection oligonucleotide of sequence

CGAGCGGCGGCC-CCAGTGTGCGGTTTCTCA (88-39), and (E) a 5' primer of sequence

AAACTGGAGGTGGGAGGGGCCTCTCG-GGAC (88-412)

a 3' primer of sequence

AGGTTCCAAATACAGCT-
CGACAAGCGGCCT (88-410)

a detection oligonucleotide of sequence

TTTCAGACTCCGATCGCAGGGTCCCTGCA
(88-411)

The present invention is directed to the above aspects and all associated methods and means for accomplishing such. For example, the invention includes techniques requisite to DNA and RNA isolation and synthesis, nucleic acid hybridization and detection, target DNA amplification and embryo (fetus) manipulation.

BRIEF DESCRIPTION OF THE DRAWINGS

FIG. 1 is a comparison of the sensitivities of bovine sexing assays using radioactively and non-radioactively labeled hybridization probes to detect amplified and unamplified male-specific DNA.

Varying concentrations of male bovine liver DNA were used as target in 25 cycles of PCR amplification. Half of the amplified samples was hybridized to $^{-}$P-labeled male-specific detection oligonucleotide 373, and exposed for 17 hours to film (panel A).

The other half of the amplified samples was hybridized to detection oligonucleotide 373 conjugated to alkaline phosphatase (AP), and then exposed to AP substrates (nitro-blue tetrazolium and 5-bromo-4-chloro-3-indolyl phosphate) (panel B).

Panel C is a 6-day autoradiogram showing various concentrations of bovine liver DNA hybridized to nick-translated, male-specific recombinant plasmids ES6, ES5(2), and ES8.

As a control, female DNA was employed (1 ng).

FIG. 2 is a comparison of the sensitivities of bovine sexing assays using radioactively labeled recombinant plasmid DNA to detect unamplified male-specific and non-sex-specific DNA, and non-radioactively labeled (alkaline phosphatase-conjugated) oligonucleotide hybridization probes to detect PCR amplified male-specific and non-sex-specific DNA. DNA was extracted from whole bovine embryos.

Panel A shows the 3-day autoradiograph of the filter hybridized to the non-sex-specific, $^{-}$P-labeled, nick-translated probe ES12.

Panel B shows the 6-day autoradiograph of the filter hybridized to the male-specific, $^{-}$P-labeled, nick-translated probes ES6, 8, and 5(2).

The filter in panel C shows the non-sex-specific amplification product obtained after 30 PCR cycles with non-sex-specific primers 88-41/88-42, detected using alkaline phosphatase-conjugated detection oligonucleotide 88-39.

The filter in panel D shows the male-specific amplification product obtained after 30 PCR cycles with male-specific primers 87-372/87-334 present, detected using alkaline phosphatase-conjugated detection oligonucleotide 87-373.

FIG. 3 is an autoradiograph showing the size of the male-specific amplified product obtained after PCR on DNA extracted from whole bovine embryos.

Ten-percent samples of the amplified products shown in FIG. 2, panels C and D were electrophoresed through a 2% agarose gel in Tris-borate buffer and the DNA from the gel was transferred to Zetaprobe (a nylon membrane) by Southern blotting in 0.4 N NaOH. The filter was hybridized to the $^{31}$P-labeled, male-specific detection oligonucleotide 87-373. As shown, a DNA product of about 210 bp was detected, as expected for the amplified product from male-specific primers 87-334/87-372.

Figure 4B:
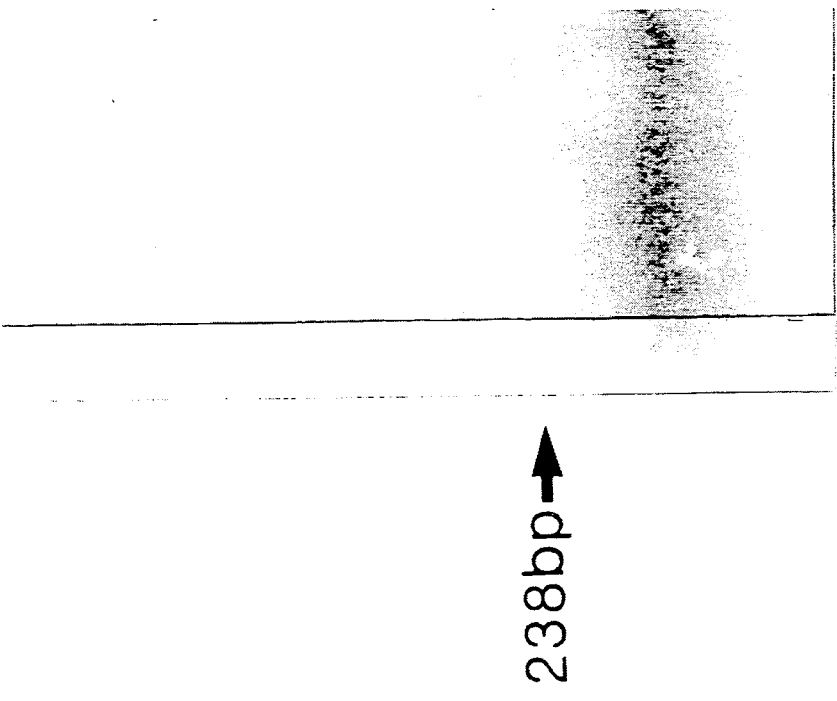
Figure 4A:
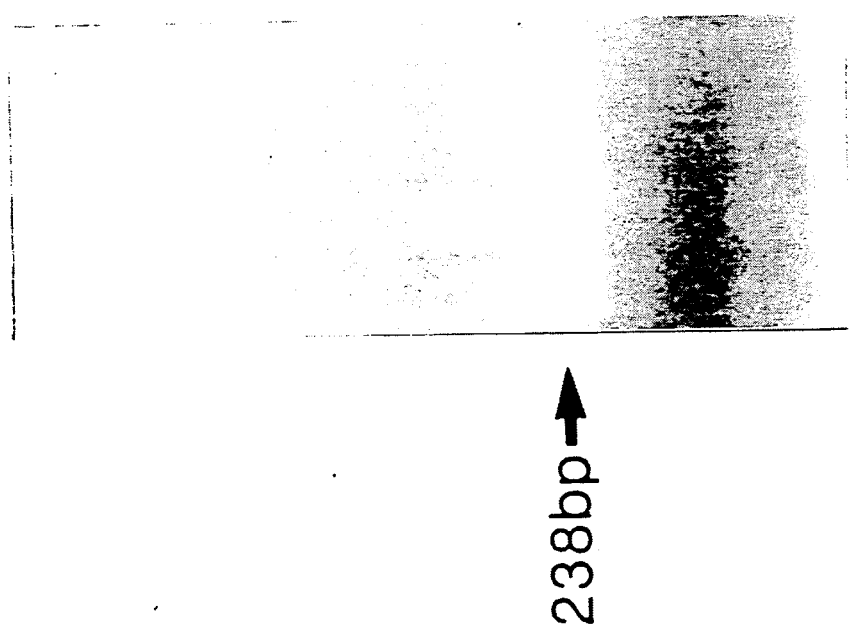

FIG. 4 shows the results of experiments performed to determine the number of PCR cycles which give quantitative amplification of the non-sex-specific amplified product. Varying quantities of male bovine liver DNA (expressed as cell number equivalents) were amplified by PCR in the presence of both non-sex-specific (88-410/88-412) and male-specific (87-334/87-372) primers. Ten-percent samples of the amplification reaction were taken after 20 and 25 cycles of PCR amplification. The samples were electrophoresed on 2% agarose gels in Tris-borate, EDTA buffer, stained with ethidium bromide, and visualized under UV irradiation.

FIG. 5 is a comparison of the PCR amplification-based sexing assay using crude lysates from whole bovine embryos and the direct hybridization assay. Whole embryo samples were divided into quarters. The DNA from one quarter of the samples was extracted and assayed using the direct hybridization assay described in the examples.

Panel A shows the 3-day autoradiograph of the filter hybridized to the non-sex-specific, $^{32}$P-labeled, nick-translated probe ES12. The amount of DNA can be estimated using the male bovine liver DNA standards (2.5-25 cell equivalents) assayed at the same time.

Panel B shows the 5.5-day autoradiograph of the filter hybridized to the male-specific, $^{32}$P-labeled, nick-translated probes ES6, ES8 and ES5(2).

Another quarter of the embryo samples was used directly in the PCR amplification-based assay. Ten-microliter samples of the amplification reaction were taken after 20 and 25 cycles of PCR. Each sample was slot-blotted to nitrocellulose filters.

The filter in Panel C contains the 20-cycle samples and shows the non-sex-specific amplification product detected using the non-radioactive, alkaline phosphatase-conjugated detection oligonucleotide 88-411. The filter in panel C contains the 25-cycle sample and shows the male-specific amplification product detected using the non-radioactive, alkaline phosphatase, male-specific detection oligonucleotide 87-373.

As controls, 10% samples from amplification reactions using 2-20 cell equivalents of purified male bovine liver DNA or 100 cell equivalents of female DNA are also shown on each filter in panels C and D.

DETAILED DESCRIPTION OF THE INVENTION

1. Definitions

The term "oligonucleotide" as used throughout the specification and claims refers to single-stranded or double-stranded DNA or RNA or hybrids between DNA and RNA that may be isolated from a natural source, may be synthesized or produced by restriction digest. The sequences of a DNA and an RNA are the same if every deoxyribonucleotide, except thymidylate, in the DNA is replaced with the corresponding ribonucleotide in the RNA and every thymidylate in the DNA is replaced with uridylate in the RNA.

Single-stranded oligonucleotides have "substantially the same sequence", within the meaning of the present invention, as the specific nucleotide sequences recited in the specification and in the claims, if they hybridize specifically with all or part of the complement of the respective specific sequences. Double-stranded oligonucleotides have "substantially the same sequence" as the illustrated specific nucleotide sequences, if either of their strands has "substantially the same sequence" within the meaning of the above definition. For example, sequences that differ in one or more nucleotides from the respective specific nucleotide sequences are considered to have "substantially the same sequence". Such variants may arise by virtue of spontaneous mutations, deletions or insertions, or alternatively, may be artificially produced, for example by site-directed mutagenesis, deletion or addition of certain nucleotides. Typically, two nucleotide sequences that are "substantially the same" do not differ in more than about 30%, preferably about 15% of the total number of nucleotides. Oligonucleotides that contain the specific nucleotide sequences recited in the specification and claims or sequences that are "substantially the same" as part of a longer oligonucleotide chain are also within the scope of the invention.

The terms "hybridization probe" and "detection oligonucleotide" are used interchangeably, and refer to an oligonucleotide (isolated from a natural source, synthetically produced or a product of restriction digest) that is capable of hybridizing with a male-specific nucleotide sequence. The hybridization probe and a corresponding male-specific nucleotide sequence have complementary or nearly complementary sequences, or contain segments with such sequences. The physical basis for hybridization is base-pairing between such complementary or nearly complementary sequences.

For use in the sex determination assay, the hybridization probes of the present invention are detectably labeled, using any reporter element that is capable of generating a detectable signal. Such detectable labels include radioactive markers such as $^{32}P$, $^{3}H$, $^{14}C$, or $^{125}I$, and non-radioactive markers, such as alkaline phosphatase, biotin, bromodeoxyuridine, fluorescent or chromogenic molecules, etc.

As known in the art of hybridization probes, oligonucleotides with different sequences may, under the same conditions, hybridize detectably to the same target nucleic acid. Two nucleic acids hybridize detectably, under stringent conditions over a sufficiently long period of time, because one of them (oligonucleotide probe) comprises a segment of at least about 10 oligonucleotides the sequence which is complementary or nearly complementary to the sequence of at least one segment in the other (target). If the time during which hybridization is allowed to occur is held constant, at a value during which, under preselected stringency conditions, two nucleic acids with exactly complementary base-pairing segments hybridize detectably to each other, increasing departures from exact complementarity can be introduced into the base-pairing segments, but base-pairing will nonetheless occur to an extent sufficient to make hybridization detectable. Furthermore, segments outside the base-pairing segments of an oligonucleotide probe, can be changed completely, without substantially diminishing the extent of hybridization between the probe and the target, if the change does not introduce a segment that is complementary or nearly complementary to a segment of another nucleic acid present in the samples to be probed.

The terms "Y-chromosome-specific DNA sequences" and "male-specific DNA sequences" are used interchangeably, and refer to DNA sequences that can be used for identifying DNA of male origin. These sequences are thought to be present only on the Y-chromosome. For practical reasons, usually repetitive Y-chromosome-specific sequences are used for identification purposes that are entirely male-specific, i.e. are not only an enrichment of repetitive sequences in the male genome compared to the female genome.

2. Materials and General Methods

Oligonucleotides. The oligonucleotides according to the invention can be synthesized and purified by any method known in the art, for example, using the solid phase cyanoethayl phosphoramidite method and HPLC purification [Gosch et.al., *Nucl. Acids Res.* 15, 5353 (1987)]. Alternatively, they can be isolated from natural sources, for example from the clone ES6 identified hereinbelow, or produced synthetically or by restriction enzyme cleavage, and, if desired, tailored so as to be suitable for the intended use.

Embryo Samples. Bovine whole embryos and embryo biopsies were obtained from Granada Genetics, Inc. TX, U.S.A.

DNA Extractions. Purified bovine male or female DNA was isolated from liver tissue by incubation with 400 µg/ml proteinase K and 1% SDS, followed by phenol/chloroform extraction and CsCl purification, to use for standardization of the assays. Nine picograms of bovine DNA are approximately equivalent to the amount of DNA in one bovine cell.

DNA was extracted from whole bovine embryos or embryo biopsies using a modification of the lysis procedure of Li et.al., *Nature* 335: 414 (1988). Whole embryos or embryo biopsies of 1–20 cells in 10 to 20 µl of buffer containing 50 mM Tris-HCl, pH 8.3, 1.7 µM sodium dodecyl sulfate, and 50 µg/ml proteinase K in a 0.5 µl microfuge tube. The embryo samples were incubated at 37° C. for 30 minutes. The Proteinase K was inactivated by incubating the samples at 85° C. for 10 minutes.

Detectable labelinq of DNA

Detectably labeling an oligonucleotide, e.g. DNA of the invention with a radioactive isotope is conveniently carried out by nick-translating a sample of the DNA in the presence of one or more deoxynucleoside-5-triphosphates which are themselves labeled with the desired isotope.

One method of non-radioactive labeling of an oligonucleotide (DNA) is to use a protected 5' allylamine U in place of the thymidylate residue during the automated synthesis of the probe. After removal of protecting groups, the probe is modified with biotin-N-hydroxysuccinimide ester. Such detection systems are available from Molecular Biosystems, Inc., San Diego, CA. Alternatively, a transamination reaction using diamine/bisulfite chemistry can be used to effect a uracil to a modified cytosine in an oligonucleotide. This can then be derivatized by a biotin active ester. Such probes are based on binding to an avidin or streptavidin-enzyme complex, where the enzyme is usually HRP or alkaline phosphatase.

Non-radioactive labeling can also be performed by using enzymes, such as alkaline phosphatase as a detectable label. Such oligonucleotide-alkaline phosphatase conjugates are known in the art and can be prepared by conventional methods [Ghosh, et.al., *Anal. biochem*, 178:43–51 (1989)].

Direct Hybridization Assay (see Example 2)

(Radioactive labeling)

DNA to be assayed was denatured in 0.3 M NaOH at 65° C. for 30 minutes. Ammonium acetate was added to a final concentration of 1 M to neutralize the sample fractions. The sample was divided into 10% and 90% fractions, and each was slot-blotted to a nitrocellulose membrane. The filters were baked to fix the DNA. The filters containing the 90% fraction were hybridized for 16 hours under standard conditions to nick-translated, male-specific probes ES6, ES8, and ES5(2). The filter containing the 10% fraction was hybridized to $^{32}$P-labeled, nick-translated, non-sex-specific clone ES12 [PCT Patent Application WO 86/07095][The probes were nick translated using standard conditions in the presence of four $^{32}$P-deoxynucleotide triphosphates - see U.S. Pat. Specification No. 4,769,319 and Maniatis et.al., Molecular Cloning: A. Laboratory Manual, Cold Spring Harbor Laboratory Press., Cold Spring Harbor, N.Y. (1982); pp. 109-112.] After exhaustive washing under stringent conditions, the filters which were hybridized with the male-specific probe were autoradiographed with two intensifying screens at −70° C. for 6 days. The filters hybridized with the non-sex-specific probe were autoradiographed for one to five days with two screens at −70° C.

PCR Amplification-based Assay

DNA to be amplified was ethanol-precipitated and the pellet resuspended in 100 μl 1×PCR buffer (50 mM KCl, 10 mM Tris, pH 8.3, 1.5 mM MgCl$_2$, 100 μg/ml of either BSA or gelatin) containing 200 μM each dATP, dTTP, dCTP, and dGTP and 0.25 μg of each primer. The resuspended DNA was denatured by boiling for 2 minutes; the primers were annealed at 50° C. for 1 minute prior to addition of 2.5 units Taq polymerase and 50 μl mineral oil. The sample was transferred to the thermocycler, which was set for 25 cycles of 3 minutes at 72° C., 1 minute at 94° C., and 1 minute at 50° C. (or the annealing temperature indicated in the examples) each cycle. Later experiments cut the times at each temperature in a cycle in half. After amplification, two 10% samples were either slot-blotted to nitrocellulose, as described in the direct hybridization assay above, or run on 2% agarose gels in Tris-borate buffer. The gels were then blotted to Zetaprobe nylon membranes using 0.4 N NaOH for the transfer buffer. The slot-blotted filters or filters from gels were hybridized for 1 hour to either male-specific or non-sex-specific oligonucleotides. After washing, the amplified products were detected by autoradiography.

Non-Radioactive Detection of Amplified Products

The nitrocellulose filters containing the amplified products were hybridized to alkaline phosphatase-conjugated detection oligomers (50 ng/ml hybridization solution) for 1 hour at 50° C. in 5×SSC, 0.5% BSA, 0.5% polyvinylpyrrolidone and 0.1% SDS. The nitrocellulose filter was prehybridized in the same buffer for 10-30 minutes. The filters were washed 3-times in 1×SSC, 0.1% SDS, followed by 2 rinses in developing buffer (100 mM Tris, pH 9.5, 100 mM NaCl, 10 mM MgCl$_2$). Color was developed for 20 minutes to 1 hour in developing buffer containing 330 μg/ml nitrotetrazolium blue and 167 μg/ml 5-bromo-4-chloro-3-indolyl-phosphate. The reaction was stopped by washing the filter in water and then phosphate buffer.

Crude Lysis Procedure

Embryo samples were stored for several days in buffer containing 50 μg/ml proteinase K and 1.7 μM SDS or, alternatively, placed in the same buffer and heated to 37° C. for 30 min. The sample was divided into quarters. One-quarter was diluted up to 100 μl in the PCR buffer containing 4 mM DTT prior to amplification. PCR amplification was performed directly on this mixture without further purification as hereinabove described.

The preparation of plasmids pES5(2) and pES8 is described in the U.S. Pat. Specification No. 4,769,319. Viable cultures of E. coli LE392 (pES5(2)) and E. coli LE392 (pES8) have been deposited at ATCC, Rockville, Md., U.S.A., under deposit numbers 53098 and 53099, respectively. The preparation of plasmid pES6 is disclosed in the PCT Patent Application Publication No. WO 86/07095, and its ATCC deposit number is 40236. Plasmid pES12 is disclosed in PCT Patent Application WO 86/07095.

Although target amplification is illustrated by the PCR amplification procedure, other target amplification techniques, for example the so called transcription amplification system (TAS), may equally be employed. The TAS system is disclosed in the co-pending USSN 07/202,978 that is a continuing application of USSN 07/064,141; and its published counterpart is the PCT Patent Application WO 88/10315. This method involves using oligonucleotides to prime the synthesis of a double-stranded DNA copy (cDNA) of the target DNA (or RNA) sequence to be amplified. In an embodiment of TAS, one of the oligonucleotides, primer A contains, within its sequence, the T7 RNA polymerase promoter binding sequence (PBS) attached to sequences complementary to the target sequence (TCS). Elongation from this primer by reverse transcriptase results in the generation of a single-stranded cDNA containing the T7 promoter at its 5' end. A second primer oligonucleotide, primer B, is complementary to the first cDNA strand at some distance (100-300 bases) downstream of primer A. Primer B is used to initiate synthesis of the second cDNA strand, producing a double-stranded cDNA with the T7 RNA polymerase promoter attached. Incubation of the doublestranded cDNA with T7 RNA polymerase and ribonucleotide triphosphates will result in the synthesis of RNA transcripts from the cDNA. Additional amplification can be achieved by repeating TAS on the newly synthesized RNA.

Alternatively, the self-sustaining sequence replication (3SR) amplification procedure may be employed in which the TAS reaction described above is carried out in the presence of RNaseH which allows further amplification since the reaction can cycle between RNA and DNA products without the need for thermal denaturation or several additions of enzymes.

In the following, additional information is provided on various materials, as well as various abbreviations used in the present specification.

NBT: 75 mg/ml Nitroblue tetrazolium in 70% dimethyl formamide

BCIP: 50 mg/ml 5-bromo-4-chloro-3-indolyl phosphate in dimethyl formamide

1×SSC:
  0.15 M NaCl
  0.015 M Na citrate adjusted to pH 7.0 with NaOH
1×BP:
- 0.5% bovine serum albumin
- 0.5% polyvinyl pyrrolidone (MW 40,000)
- filter through a 0.45 μ nitrocellulose filter 10% SDS:
- 10 grams sodium dodecyl sulfate
- to 100 ml with deionized, distilled water developing buffer:
- 100 mM Tris-HCl, pH 9.5
- 100 mM NaCl
- 10 mM $MgCl_2$ Agarose: Bio-Rad, Inc., Chemical Division, Richmond, California, U.S.A.

Nitrocellulose filters: Schleicher and Schull, Inc. Keene, New Hampshire, U.S.A.

3. Description of a Preferred Embodiment

According to a preferred embodiment of the invention, crude lysates obtained from whole bovine embryos are used for the determination of sex. Male-specific DNA present in the crude lysates obtained as described hereinabove and as illustrated in the Examples, is amplified following the PCR amplification procedure.

In order to minimize the time required to perform the sexing assay while maintaining sensitivity, the parameters of the PCR amplification procedure can be optimized. The selection of the optimum parameters in a given experimental set is well within the knowledge of a person of ordinary skill in the art.

To choose the optimum annealing temperature, bovine male liver DNA at concentrations of 25 and 10 cell equivalents was amplified for 15 or 25 cycles of PCR using a one-minute annealing step at temperatures of 37° C., 42° C., or 50° C. The denaturing step remained 1 minute at 94° C., and the synthesis step remained 3 minutes at 72° C. There was very little difference in the amount of male-specific amplified product detected at annealing temperatures of 42° C. and 50° C., but an annealing temperature of 37° C. gave 10-fold less product after 25 cycles. A temperature of about 50° C. appears to maximize the product obtained, and in the same time, decrease thermocycler time during temperature changes.

Preferably, non-sex-specific primers are also included in the PCR amplification assay, to determine whether the sample contained DNA. However, adding non-sex-specific primers along with male-specific primers to the amplification reaction lowers the overall efficiency of the amplification such that about 30 cycles are required to detect male-specific product from one cell equivalent of DNA instead of the 20-25 cycles needed with the male-specific primers alone, otherwise under the same circumstances. The lowered PCR efficiency may be the result of competition between the two concurrent amplification reactions (non-sex-specific and male-specific) for the required enzyme, or interference of one set of primer pairs in the amplification reaction with the other primer pair. The reduction in the amplification efficiency of the male-specific product was found to be the least severe when using the non-sex-specific primers 88-410/88-412, and male-specific primers 87-334/-87-372. In this preferred combination, a 10% aliquot of one cell equivalent of male DNA could be detected in 25 cycles of PCR (using the 50 C annealing temperature), in an 8-hour exposure of an autoradiograph using a $^{32}P$-labeled detection probe.

The third parameter examined was the time required for each step in the PCR amplification cycle. The cycle time was reduced from five minutes (1 minute at 94° C., 1 minute at 50° C., and 3 minutes at 72.C) to 2.5 minutes (1.5 minutes at 72° C., 30 seconds at 94° C., and 30 seconds at 50° C.).

Preferred oligonucleotide primers according to the invention, are described in detail in the examples.

Following PCR amplification, the male-specific target DNA is preferably detected by virtue of hybridization with a detectably labeled detection oligonucleotide. Non-radioactive labels, for example, enzymes, e.g. alkaline phosphatase, are preferred. The most preferred probes according to the present invention are those that hybridize appreciable only with male DNA. With such probes, single negative control hybridization with DNA derived from a female of the same species, run in parallel with hybridization of DNA from the embryo or fetus being sexed, will generally be sufficient for ease and accuracy in sexing.

Alternatively, satisfactory results may be obtained by increasing the number of cycles to 35 and identifying the PCR-amplified product by its size, on an appropriate gel, e.g., an ethidium bromide-stained gel. The product is of the predicted size, however spurious amplification products can occur in addition to the specific product. This is an advantage of the process according to the present invention.

Further details of the invention are illustrated by the following non-limiting examples.

4. EXAMPLES

Example 1

Comparison of sensitivities of bovine sexing assays using isotopic and non-isotopically labeled hybridization probes to detect amplified and unamplified male-specific DNA The sensitivity of the bovine sexing assay carried out on DNA samples amplified by polymerase chain reaction (PCR) was determined by amplifying varying concentrations of male bovine (liver) DNA using the oligonucleotide primer pair 87-334/87-372. DNA was isolated and purified from bovine liver tissue, and the PCR amplification was performed as described in the Materials and General Methods section of the specification. Amplified product was detected, via hybridization to a $^{32}P$-labeled oligonucleotide probe, from as little as 10 picograms (one cell equivalent) of male target DNA after 25 cycles of PCR, using this primer pair. The signal generated for one cell equivalent of male DNA is at least 10-fold greater than the signal generated for 100 cell equivalents of female DNA (see FIG. 1, panel A).

The sensitivity of the amplification assay using a non-radioactive detection probe is shown in FIG. 1, panel B. Varying amounts (500 pg–10 pg) of male-specific DNA and 1 ng of female specific DNA were employed in 25 cycles of PCR amplification with the primer pair 87-334 and 87-372. The products were detected using an alkaline phosphatase (AP) conjugated oligonucleotide probe, prepared as described in the Materials and General Methods section of the specification. The AP-labeled probe was able to detect one cell equivalent of male DNA, however, the signal-to-noise ratio was not as high as that observed with the $^{32}P$-labeled probe. While the radioactive and AP-labeled probes were equally sensitive in this assay, the detection time (i.e., color development time) for the blot shown in FIG. 1, panel B was only 30 minutes, compared to an overnight exposure for the autoradiogram shown in FIG. 1, panel A.

FIG. 1, panel C illustrates the increased sensitivity using a target amplification protocol, as compared to the direct hybridization assay. The hybridization and the nick-translation procedures employed were essentially as described in the U. S. Pat. No. 4,769,319 (Example II). The whole content of the United States Patent No.4,769,319 is hereby expressly incorporated by reference. The autoradiogram shown is a 6-day exposure of a male DNA dilution series assayed by direct hybridization assay, using a nick-translated, $^{32}$P-labeled probe. The lowest concentration of male DNA in this particular blot represents 2.5 cell equivalents. The intensity of the signal is about a tenth of the signal obtained at the one-cell level using the amplification assay in a 17-hour exposure of the autoradiogram.

Example 2

Comparison of the PCR amplification and direct hybridization assays on DNA extracted from whole bovine embryos 1. Direct hybridization assay; radioactive Whole embryos, shipped in buffer containing proteinase K and 1% SDS, were obtained from Granada Genetics, Inc., TX U.S.A. The DNA was extracted with phenol/chloroform and divided into halves. One half of the DNA was assayed by the standard radioactive, direct unamplified hybridization protocol, while the other half was ethanol-precipitated and assayed by the amplification-based and non-radioactive assay. A detailed description of these procedures is given in the Materials and General Methods section.

FIG. 2 shows the sexing results obtained from both the direct hybridization and amplification-based assays. The results of the direct hybridization assay are shown in panels A and B. The filter in panel A was hybridized to the $^{32}$P-labeled non-sex-specific probe (ES12), which allows the initial amount of DNA in each sample to be determined when compared to the male DNA standards included on the same filter. The filter shown in panel B was hybridized to a combination of three $^{32}$P-labeled male-specific probes (ES6.0, ES5(2), and ES8). The embryo samples are numbered 11 through 17. The DNA from embryos #16 and #17 was diluted serially by 2-fold dilutions prior to being assayed to allow the sensitivity of the assays to be determined. Embryo sample #11 did not contain DNA, since no signal was detected with the non-sex-specific probe (panel A). Embryo samples #13, #14, #15, and #17 were female, while embryo samples #12 and #16 were male.

2. Amplification-based assay; non-radioactive

FIG. 2, panels C and D, show the sexing results obtained with PCR-amplification of the target embryonic DNA. Two sets of oligonucleotide primers were included during the PCR amplification. The first set of primers consisted of the male-specific oligonucleotides 87-334 and 87-372. The second set of primers consisted of the non-sex-specific oligonucleotides 88-41 and 88-42, which are complementary to bovine satellite DNA sequences. The non-sex-specific primers were included to determine whether the sample contained DNA. The filter in panel C was hybridized to alkaline phosphatase-conjugated oligonucleotide 88-39, which can detect the non-sex-specific amplified product of primers 88-41/88-42. The filter in panel D was hybridized to the alkaline phosphatase-conjugated male-specific detection oligonucleotide 87-373, which detects the amplified product from primers 87-334/-87-372. The DNA extracted from embryo samples #16 and #17 was diluted as in the experiment without PCR amplification. The sexing results of the amplification-based assay agree with the results obtained in the direct hybridization assay. Embryo sample #11 contained no DNA, embryo samples #12 and #16 were male, and the rest of the embryos were female.

3. Sensitivity

The sensitivity of the direct hybridization and amplification-based assays determined by probe hybridization to the male bovine liver DNA standard (9 picograms of DNA equaling one cell equivalent) were less than the sensitivities estimated from the diluted embryo DNA sample. In the direct hybridization assay applied to embryos, the sensitivity was only five cell equivalents on the male DNA (FIG. 2, panel B). However, a signal was detected in the 1/32nd dilution (or 1/64th of the DNA from an entire embryo) of embryo #16, which gives a sensitivity of 1.25 cell equivalents, assuming that an embryo contains about 80 cells. In the assay carried out on PCR-amplified embryo targets, the sensitivity was 10% of two cell equivalents based on the male DNA standard (only 1/10th of the sample was used in the blot; FIG. 2, panel D). In contrast, a male-specific signal could detected in the 1/64th dilution of embryo #16 (1/128th of the whole embryo), and since only a tenth of the amplification reaction was used in the hybridization, the sensitivity of the amplification protocol in this experiment was less then one (0.0625) cell equivalent using embryo #16 as the reference. These discrepancies in the estimated sensitivities using different reference standards are probably due to the degradation of the male liver DNA used as standard, resulting in lowered hybridization competency.

The results of both sensitivity estimates indicate that the non-radioactive amplification-based assay is more sensitive than the direct hybridization assay. The PCR-amplification-based protocol allows the sex of an embryo to be determined using a non-isotopic detection method starting with a one-cell embryo biopsy.

Example 3

Characterization of the PCR-amplified DNA products

The products of the reactions described in Example 2, Step 2 (FIG. 2, panels C and D), were analyzed on agarose gels to determine the size of the PCR-amplified products. The amplified product from non-sex-specific primers 88-41 and 88-42 was visualized by ethidium bromide staining and UV irradiation (data not shown). The amplification product was the expected 262 bp DNA fragment. The amplification product of the male-specific primers was detected by Southern transfer and hybridization to $^{32}$P-labeled oligonucleotide 87-373. The results are shown in FIG. 3. A 210 bp DNA product was detected from embryos #12 and #16. The band that appears slightly below the 210 bp DNA band in FIG. 3 most likely represents a male-specific product that is not fully double-stranded, which accounts for its slightly different migration pattern in the gel. Very slight hybridization to the male-specific probe was detected in the ¼ and 1/32 dilution samples shown in FIG. 2D. The intensity of this band is much less than the intensity of the male-specific bands detected in the embryo #16 dilution series (see also FIG. 2, panel D).

Example 4

Quantitation of the amplification-based assay

In the direct hybridization assay, the use of the non-sex-specific probe not only determines whether the DNA is present in the sample, but also provides a means of estimating the initial cell number. In the amplification-based assay, 25 cycles of PCR will also determine the presence or absence of DNA in the sample, but it does not necessarily reflect the initial cell number, as shown in FIG. 4, panel A. Once the amount of amplification product reaches a certain level, the efficiency of amplification drops. If, however, fewer cycles of PCR are performed, the amount of non-sex-specific product becomes proportional to the initial DNA concentration or cell number in the range of concentrations used for these experiments, as shown in FIG. 4, panel B. This range of cell numbers (2–25) is the usual range of cells used for the sexing assay. These results show that in order to make the amplification-based assay quantitative for the non-sex-specific product, the number of PCR cycles must be limited to 20 cycles or less.

Example 5

Amplification on crude lysates from embryo samples

The amplification-based assay including the crude lysis procedure is the preferred mode and has been used on embryo samples. Whole embryos shipped in SDS and proteinase K buffer were obtained from Granada Genetics, Inc., TX, U.S.A. The embryonic samples were split into quarters. The DNA from one quarter sample was phenol/chloroform extracted and assayed by the direct hybridization assay, as shown in FIG. 5, panels A and B. To another quarter of the embryo sample was added PCR buffer plus DTT (see crude lysis procedure (p. 16)) and assayed by the amplification-based assay without further purification. The PCR-amplification-based assay (see p. 16) was performed following a modified protocol using the optimized parameters described in the description of a Preferred Embodiment section of the specification, i.e., denaturation was at 94° C. for 0.5 min, annealing was at 50° C. for 0.5 min, and synthesis was at 72° C. for 1.5 min for PCR cycles following the initial 2 min denaturation step with Taq enzyme addition. Aliquots were taken after 20 and 25 cycles of PCR and slot-blotted to nitrocellulose. The 20-cycle sample was hybridized to the alkaline phosphatase-conjugated probe 88–411, which detects the non-sex-specific amplified product from primer pair 88–410/88–412. The results are shown in FIG. 5, panel C. The 25-cycle sample was hybridized to the alkaline phosphatase-conjugated, oligonucleotide probe 87–373, which detects the male-specific amplified product from primer pair 87–334/87–372. The results are shown in FIG. 7, panel D. The standard curve of male DNA used as a control in this experiment was made with purified DNA and not crude lysates of male cultured cells. Direct determination of the sensitivity of the assay on crude lysates cannot be made using the purified male DNA standard. However, if the original whole embryo sample contained approximately 80 cells, the sample on the filters shown in panels C and D represents 10% aliquots of 20 cells, or about two cell equivalents. The embryo sexing results obtained by the two different assays agree. Embryos E2, E6, E7, E8, E10, E13, and E14 were male. Embryos E1, E3, E4, E5, E9, E11, and E12 were female.

We claim:

1. An oligonucleotide having or containing substantially the same sequence as that of a DNA selected from the group consisting of

CCTTGCACAGTCGCTAGGGCACA,

ATCCAGGCTGGCTCCTGCCCTCGGTCAAGA and

GTTCCGCCCTTCCTGAAGTGCCCGTCTAAA.

2. An oligonucleotide according to claim 1 which is labeled with a detectable marker.

3. An oligonucleotide according to claim 2 wherein said detectable marker is selected from the group consisting of $^3H$, $^{32}P$, alkaline phosphatase and biotin.

4. An oligonucleotide according to claim 3 wherein said detectable marker is alkaline phosphatase.

5. A method for determining the sex of an embryo or fetus of a species of genus Bos, comprising:
(a) contacting chromosomal DNA extracted from at least 100 cells of said embryo or fetus under hybridization conditions with one or more hybridization probes labeled with a detectable market, at least one of said probes having or containing substantially the same sequence as that of a male-specific DNA selected from the group consisting of

CCTTGCACAGTCGCTAGGGCACA,

ATCCAGGCTGGCTCCTGCCCTCGGT-CAAGA and

GTTCCGCCCTTCCTGAAGTGCCCGT-CTAAA, and
(b) ascertaining whether hybridization above background occurs between said chromosomal DNA and said male-specific occurs between said chromosomal DNA and said male-specific hybridization probe or probes.

6. A method according to claim 5, wherein said detectable marker is selected from the group consisting of $^3H$, $^{32}P$, alkaline phosphatase and biotin.

7. A method according to claim 6 wherein said detectable marker is alkaline phosphatase.

8. A method for determining the sex of an embryo or fetus of a species of genus Bos, comprising:
(a) amplifying a male specific segment of chromosomal DNA of said embryo or fetus, by
  (i) separating complementary strands of said chromosomal DNA,
  (ii) annealing the separated complementary strands, respectively with a 5′ and 3′ oligonucleotide primer pair having sufficient homology with said strand of male-specific segment of said chromosomal DNA to hybridize therewith,
  (iii) incubating the annealed DNA with DNA polymerase whereby the 5′ and 3′ oligonucleotide primers are extended through said male-specific segment of said chromosomal DNA, if present, and repeating steps (a) (i)-(iii) as many times as required to obtain a desired level of said double-stranded male-specific segment of said chromosomal DNA, and (b) detecting the amplified, double-stranded male-specific segment in said chromosomal DNA by
  (i) contacting said chromosomal DNA under hybridization conditions with a hybridization probe labeled with a detectable marker, and
  (ii) ascertaining whether hybridization above background occurs between said chromosomal DNA of the embryo or fetus and the hybridization probe, wherein said 5' and 3' oligonucleotide pair and said hybridization probe have or contain substantially the same sequences as those of the DNAs selected from the group consisting of (A) a 5' primer of sequence

CACAGTCGCCAGGGCACAGGGCTG a 3' primer of sequence

AGCCCTGTGCTCTGGCGACTGTGAAACC a detection oligonucleotide of sequence

CCTTGCACAGTCGCTAGGGCACA, (B) a 5' primer of sequence

AAGACCCTGACAAACACTCCTGAGC-CCACC a 3' primer of sequence

GCCTGCTTCGGTGCAGGGATCC-GGAGTGGG a detection oligonucleotide of sequence

ATCCAGGCTGGCTCCTGCCCTCGGT-CAAGA, (C) a 5' primer of sequence

CCTCCCCTTGTTCAAACGCCCGGAAT-CATT a 3' primer of sequence

TGCTTGACTGCAGGGACC-GAGAGGTTTGGG a detection oligonucleotide of sequence

GTTCCGCCCTTCCTGAAGTGCCCGT-CTAAA.

9. A method according to claim 8, wherein in step (a) a non-sex-specific DNA segment is also coamplified, using non-sex-specific 5' and 3' primers and a detection oligonucleotide selected from the group consisting of (D) a 5' primer of sequence

AGGTCGCGAGATTGGTCGCTAGGT-CATGCA a 3' primer of sequence

AAGACCTCGAGAGACCCTCTTCAACACGT a detection oligonucleotide of sequence

CGAGCGGCGGCC-CCAGTGTGCGGTTTCTCA, (E) a 5' primer of sequence

AAACTGGAGGTGGGAGGGGCCTCTCG-GGAC a 3' of sequence

AGGTTCCAAATACAGCT-CGACAAGCGGCCT a detection oligonucleotide of sequence

TTTCAGACTCCGATCGCAGGGTCCCTGCA.

10. A method according to claim 8, wherein said detectable marker is selected from the group consisting of $^3$H, $^{32}$P, alkaline phosphatase and biotin.

11. A method according to claim 10 wherein said detectable marker is alkaline phosphatase.

* * * * *

UNITED STATES PATENT AND TRADEMARK OFFICE
CERTIFICATE OF CORRECTION

PATENT NO. : 5,055,393

DATED : October 8, 1991

INVENTOR(S) : Kwoh, et al.

It is certified that error appears in the above-identified patent and that said Letters Patent is hereby corrected as shown below:

On Title page : [73] Assignee, before "Salk" insert --The--; [56] References Cited, U.S. Patent Documents, line 1, after "Mullis et al." insert the class/subclass --435/6--; [56] References Cited, Foreign Patent Documents, add cited classes and subclasses as follows: --C12Q 1/68; C12Q 1/68; C12Q 1/68; C07H 21/04--; [56] Other Publications, under Bondioli et al., line 3, change "Therigenology" to --Theriogenology--; [56] Other Publications, under Herr et al., line 6, change "rapid" to --Rapid--; <u>IN THE SPECIFICATION</u>: Column 2, line 16, change "of" (second occurrence) to --bp--; Column 2, line 57, change "of" to --bp--; Column 3, line 9, change "84-151)" to --(87-151)--; Column 3, line 32, delete the entire line and insert in its place --ATCCAGGCTGGCTCCTGCCCTCGGTCAAGA (87-371)--; Column 4, line 26, after "a 3' primer of sequence", on the next line insert --GCCTGCTTCGGTGCAGGGATCCGGAGTGGG (87-370)--; Column 5, line 24, change "$^-$P" to --$^{32}$P--; Column 5, line 46, change "$^-$P" to --$^{32}$P--; Column 5, line 49, change "$^-$P" to --$^{32}$P--; Column 6, line 1, change "$^{31}$P" to --$^{32}$P--; Column 9, line 66, change "MgClz" to --$MgCl_2$--; Column 10, line 35, change "A" to --<u>A</u>--; Column 10, line 42, change "B" to --<u>B</u>--; Column 10, line 44, change "A" to --<u>A</u>--; Column 10, line 47, change "doublestranded" to --double-stranded--; Column 11, line 68, change "50 C" to --50°C--; Column 12, line 6, change "72.C" to --72°C--;

UNITED STATES PATENT AND TRADEMARK OFFICE
CERTIFICATE OF CORRECTION

PATENT NO. : 5,055,393

DATED : October 8, 1991

INVENTOR(S) : Kwoh, et al.

It is certified that error appears in the above-identified patent and that said Letters Patent is hereby corrected as shown below:

IN THE CLAIMS: Column 16, line 28, change "amrket" to --marker--; Column 16, lines 44-45, after "male-specific" delete "occurs between said chromosomal DNA and male-specific--; Column 17, line 40, after the sequence, insert --and--; Column 18, line 11, change "coamplified" to --co-amplified--; Column 18, line 32, after "3'" insert --primer--.

Signed and Sealed this

Thirteenth Day of July, 1993

Attest:

MICHAEL K. KIRK

Attesting Officer

Acting Commissioner of Patents and Trademarks